(12) United States Patent
Izumi et al.

(10) Patent No.: US 6,875,878 B2
(45) Date of Patent: Apr. 5, 2005

(54) CHROMENE COMPOUND

(75) Inventors: Shinobu Izumi, Yamaguchi-ken (JP); Hironobu Nagoh, Yamaguchi-ken (JP)

(73) Assignee: Tokuyama Corporation, Yamaguchi (JP)

( * ) Notice: Subject to any disclaimer, the term of this patent is extended or adjusted under 35 U.S.C. 154(b) by 2 days.

(21) Appl. No.: 10/466,214
(22) PCT Filed: Nov. 15, 2002
(86) PCT No.: PCT/JP02/11935
§ 371 (c)(1), (2), (4) Date: Jul. 14, 2003
(87) PCT Pub. No.: WO03/042203
PCT Pub. Date: May 22, 2003

(65) Prior Publication Data
US 2004/0242856 A1 Dec. 2, 2004

(30) Foreign Application Priority Data
Nov. 16, 2001 (JP) ........................ 2001-352333

(51) Int. Cl.$^7$ ...................... C07D 311/78; C07D 311/94
(52) U.S. Cl. .................. 549/381; 430/270.15
(58) Field of Search ......................... 549/381

(56) References Cited

U.S. PATENT DOCUMENTS 4,578,469 A * 3/1986 Deger et al. ................... 546/66

FOREIGN PATENT DOCUMENTS

| WO | 00/15628 | * | 5/2000 |
| WO | 00/77007 | * | 12/2000 |
| WO | 02/090342 | * | 11/2002 |

* cited by examiner

Primary Examiner—Taofiq Solola
(74) Attorney, Agent, or Firm—Sherman & Shalloway

(57) ABSTRACT

A chromene compound represented by the general formula (1),

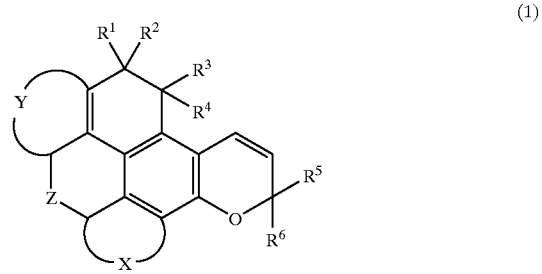

(1)

wherein $R^1$ to $R^4$ are hydrogen atoms, hydroxyl groups, alkyl groups, alkoxy groups, substituted amino groups or halogen atoms, $R^1$ to $R^4$ may be bonded together to form a ring, $R^5$ and $R^6$ are alkyl groups, aryl groups or heteroaryl groups, or $R^5$ and $R^6$ together may form a ring, a cyclic group containing X or Y is an aromatic hydrocarbon group or an aromatic heterocyclic group, and a divalent group Z is an alkylene group.

This compound exhibits excellent photochromic properties, such as small initial color, a large fading rate, excellent resistance and developing a color tone of a neutral tint.

11 Claims, 1 Drawing Sheet

CHROMENE COMPOUND

This application is a 371 of PCT/JP02/11935 filed Nov. 15, 2002.

TECHNICAL FIELD

The present invention relates to a novel chromene compound and to the use of the chromene compound.

BACKGROUND ART

Photochromism is a phenomenon that is drawing attention in recent several years and is a reversible action of a compound which quickly changes its color (called color development) when it is irradiated with light containing ultraviolet rays such as sunlight or light of a mercury lamp and resumes its initial color (called color fading) when it is no longer irradiated with light but is placed in a dark place. The compound having this property is called photochromic compound. One of the applications of the photochromic compound may be a dimmer material for lenses of sunglasses.

When used for the above application, the photochromic compound must satisfy the following photochromic properties:

① Color changes stably when the color development and color fading are repeated (favorably resistance the repetition).
② Has a small coloring degree in a state of not irradiated with light (has a small initial color).
③ Exhibits a quick fading rate when the irradiation with light is discontinued.

In recent years, further, it has been desired to realize a compound which is capable of developing a neutral tint such as grey, brown or green. The compound that develops such a neutral tint must have two absorption bands (420 to 520 nm and 520 to 620 nm) of nearly the same absorption intensities in the wavelength region of visible rays.

In order to satisfy the above requirements, there have heretofore been synthesized a variety of photochromic compounds without, however, any common nature in their structures.

U.S. Pat. No. 5,783,116 discloses a chromene compound represented by the following formula (A),

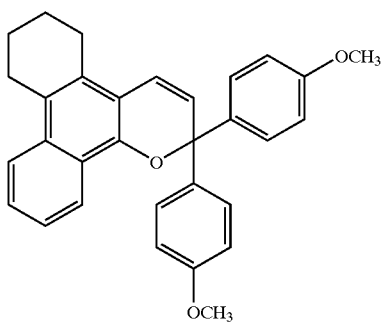

(A)

This chromene compound, however, has only one absorption band. Therefore, this chromene compound is not capable of developing a color tone of a neutral tint and, besides, exhibits a slow fading rate.

Further, PCT Patent Application WO00/15628 discloses a chromene compound represented by the following formula (B),

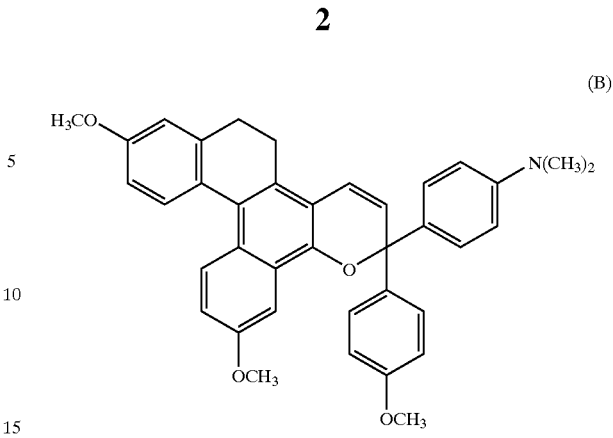

(B)

To satisfy the requirement of coloring spectrum of the above-mentioned neutral tint, this chromene compound develops a neutral tint of brown color while developing a small initial color involving, however, a problem of a slow fading rate.

The present inventors have previously discovered a chromene compound represented by the following general formula (C) among the compounds disclosed in their patent application (Japanese Unexamined Patent Publication (Kokai) 11-154272).

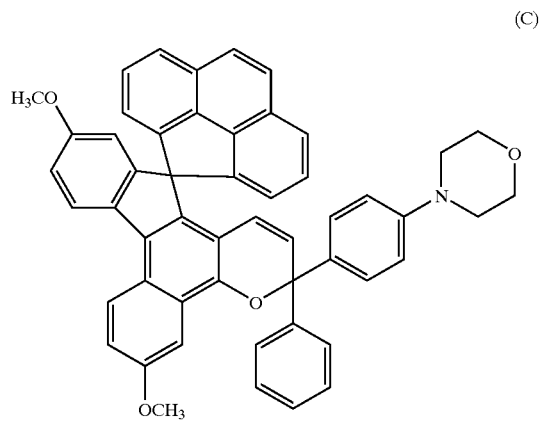

(C)

This chromene compound exhibits a large fading rate. Due to a large difference in the absorption intensity between the two absorption bands, however, this chromene compound is capable of developing a single blue color only.

DISCLOSURE OF THE INVENTION

It is therefore an object of the present invention to further improve photochromic properties of the conventional compounds while solving their problems. Namely, the present invention provides a chromene compound that exhibits a small initial color, a large fading rate, a good resistance and that develops a color tone of a neutral tint.

Namely, the present invention provides a chromene compound represented by the following formula (1),

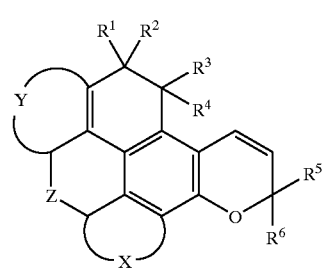

(1)

wherein $R^1$, $R^2$, $R^3$ and $R^4$ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups or halogenoalkoxy groups, $R^1$ and $R^2$ together, and $R^3$ and $R^4$ together, may form rings, and either $R^1$ or $R^2$ and either $R^3$ or $R^4$ together may form a ring, $R^5$ and $R^6$ are, independently from each other, alkyl groups, substituted or unsubstituted aryl groups, or substituted or unsubstituted heteroaryl groups, or R5 and R6 together may form a ring, a trivalent cyclic group represented by the following formula (2),

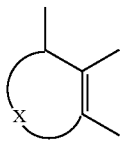

(2)

and a trivalent cyclic group represented by the following formula (3),

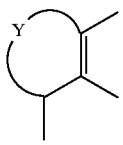

(3)

are, independently from each other, substituted or unsubstituted aromatic hydrocarbon groups or substituted or unsubstituted aromatic heterocyclic groups, and a divalent group Z is the one presented by the following formula (4) or (5),

(4)

(5)

wherein $R^7$, $R^8$ and $R^9$ are, independently from each other, alkylene groups, B and B' are, independently from each other, imino groups, substituted imino groups, oxy groups, thio groups, carbonyl groups, cycloalkylene groups, cycloalkylidene groups, or substituted or unsubstituted arylene groups, and m, n, p and q are 0 or 1.

According to the present invention, further, there are provided a photochromic material comprising a chromene compound represented by the above general formula (1), and a photochromic optical material containing the chromene compound.

BEST MODE FOR CARRYING OUT THE INVENTION

Figure 1:
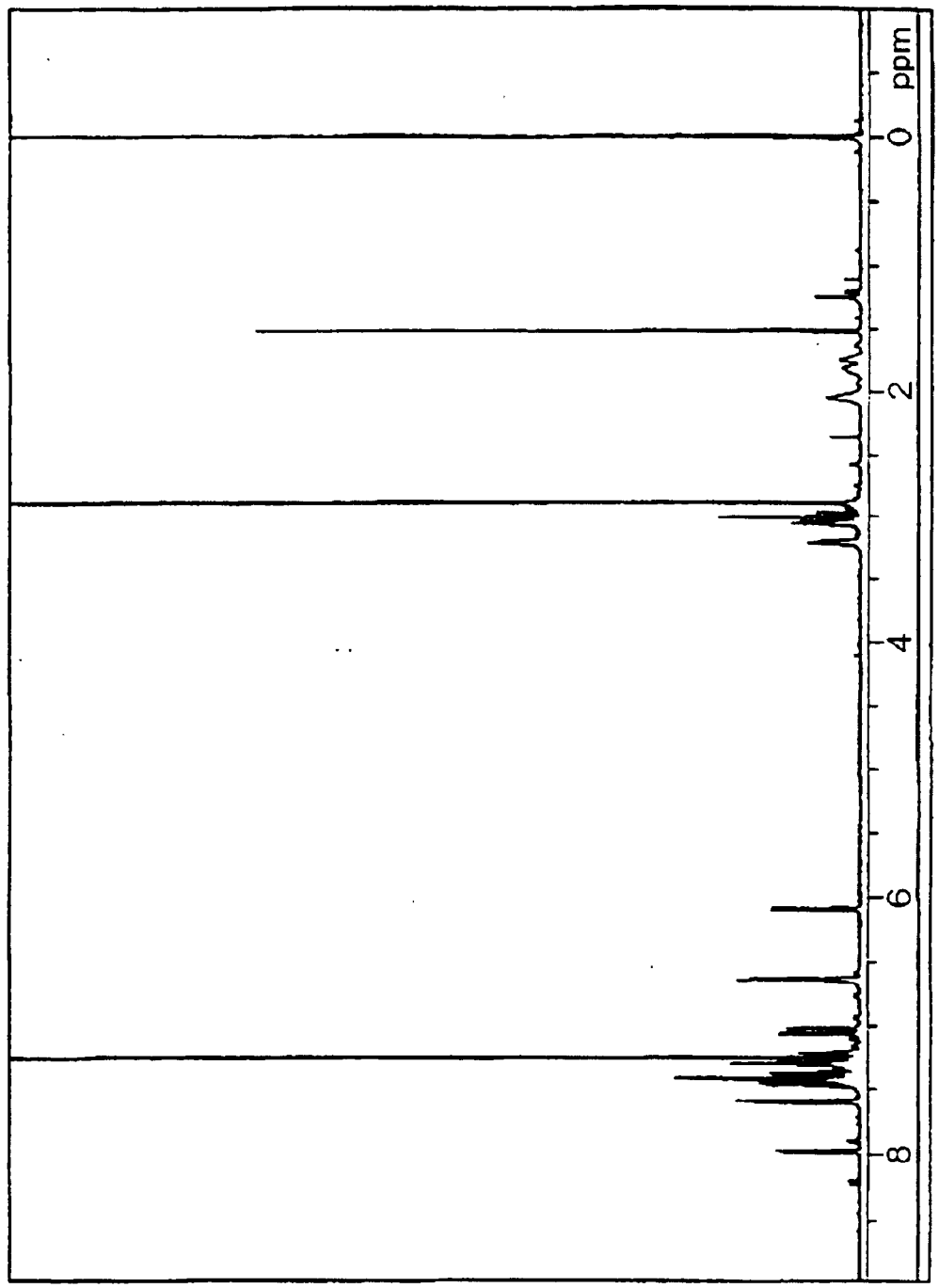
FIG. 1 is a diagram of a proton nuclear magnetic resonance spectrum of a compound of Example 1.

Described below are the groups in the above-mentioned general formula (1).

Trivalent Cyclic Groups [Formulas (2) and (3)]

The trivalent cyclic groups represented by the following formulas (2) and (3),

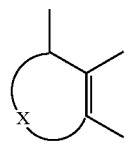

(2)

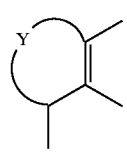

(3)

in the above-mentioned general formula (1) are, independently from each other, substituted or unsubstituted aromatic hydrocarbon groups, or substituted or unsubstituted aromatic heterocyclic groups.

Though there is no particular limitation, the aromatic hydrocarbon groups are preferably those having 6 to 18 carbon atoms (without including carbon atoms of the substituent). As the preferred aromatic hydrocarbon groups, there can be exemplified trivalent groups derived from a benzene ring, such as benzene, naphthalene and phenanthrene, and trivalent groups derived from a condensed ring formed by the condensation of 2 to 4 benzene rings. A trivalent group derived from a benzene ring is particularly desired.

Though there is no particular limitation, it is desired that the aromatic heterocyclic group is a trivalent group comprising an aromatic heterocyclic ring selected from a 5-membered ring or a 6-membered ring containing oxygen atom, sulfur atom or nitrogen atom; a condensed heterocyclic ring in which the above 5-membered or 6-membered heterocyclic ring is condensed with a benzene ring; or a condensed heterocyclic ring in which the aromatic hydrocarbon ring such as benzene ring is condensed with the above heterocyclic ring of the 5-membered ring or the 6-membered ring. As a preferred aromatic heterocyclic ring, there can be exemplified trivalent groups derived from a nitrogen-containing heterocyclic ring, such as pyridine, quinoline, dihydroquinoline, pyrrole and indole; trivalent groups derived from an oxygen-containing heterocyclic ring, such as furane and benzofurane; and trivalent groups derived from a sulfur-containing heterocyclic ring, such as thiophene and benzothiophene.

The above-mentioned aromatic hydrocarbon groups and the aromatic heterocyclic groups may have a substituent (hereinafter written as Rsb).

As the substituent (Rsb), there can be exemplified hydroxyl group; alkyl group; cycloalkyl group; alkoxy group; aralkyl group; aralkoxy group; amino group; substituted amino group; cyano group; nitro group; substituted or unsubstituted aryl group; substituted or unsubstituted heteroaryl group; halogen atom; halogenoalkyl group; halogenoalkoxy group; and substituted or unsubstituted heterocyclic group having a nitrogen atom as a hetero atom, and is bonded to the aromatic hydrocarbon group or to the aromatic heterocyclic group via the nitrogen atom (this heterocyclic group may further form a condensed heterocyclic group being condensed with an aromatic hydrocarbon ring or an aromatic heterocyclic ring).

Further, the substituent (Rsb) may be a group represented by the following formula (6) or (7),

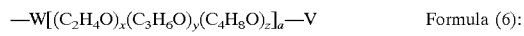

Formula (6):

wherein W is —C(=O)O—, —CH$_2$O—, —OC(=O)—, —N(R$^a$)C(=O)—, —N[C(=O)—]$_2$, —N(R$^a$)—, —N(R$^a$)CON(H)—, >N—, an oxygen atom or a sulfur atom, x, y and z are integers of 0 to 50, the total number of x, y and z is 1 to 50, a is 1 when W is —C(=O)O—, —CH$_2$O—, —OC(=O)—, —N(R$^a$)C(=O)—, —N(R$^a$)—, —N(R$^a$)CON(H)—, an oxygen atom or a sulfur atom, and is 2 when W is —N[C(=O)—]$_2$ or >N—, V is a hydrogen atom, a (meth)acryloyl group, a group having an epoxy group with 1 to 5 carbon atoms, a group having a carboxyl group with 1 to 5 carbon atoms, an oxorane group, an aminoalkyl group with 1 to 6 carbon atoms or an oxylanylmethyl group, and R$^a$ is a hydrogen atom or an alkyl group having 1 to 20 carbon atoms,

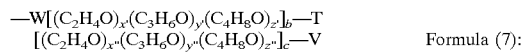

Formula (7):

wherein, T is a divalent organic residue having 5 to 20 carbon atoms and containing a cyclic group, W and V are as defined in the formula (6), x', y', z', x", y" and z" are the same as x, y and z in the formula (6).

The above-mentioned substituent (Rsb) will now be described.

Though there is no particular limitation, the alkyl group is usually the one having 1 to 4 carbon atoms. Preferred examples of the alkyl group include methyl group, ethyl group, n-propyl group, isopropyl group, n-butyl group, sec-butyl group, and tert-butyl group.

Though there is no particular limitation, the cycloalkyl group is usually an alkyl group having 3 to 12 carbon atoms. Preferred examples of the alkyl group include cyclopropyl group, cyclobutyl group, cyclopentyl group, cyclohexyl group, cycloheptyl group and cyclooctyl group.

Though there is no particular limitation, the alkoxy group is usually the one having 1 to 5 carbon atoms. Concrete examples of the preferred alkoxy group include methoxy group, ethoxy group, n-propoxy group, isopropoxy group, n-butoxy group, sec-butoxy group and tert-butoxy group.

Though there is no particular limitation, the aralkyl group is usually the one having 7 to 11 carbon atoms. Preferred examples of the aralkyl group include benzyl group, phenylethyl group, phenylpropyl group and phenylbutyl group.

Though there is no particular limitation, it is desired that the aralkoxy group is the one having 6 to 10 carbon atoms. Preferred examples of the aralkoxy group include phenoxy group and naphthoxy group.

Though there is no particular limitation, the substituted amino group is an amino group having an alkyl group or an aryl group as the substituted group, such as an alkylamino group, a dialkylamino group, an arylamino group or a diarylamino group. Concrete examples of the preferred substituted amino group include methylamino group, ethylamino group, phenylamino group, dimethylamino group, diethylamino group and diphenylamino group.

Though there is no particular limitation, the unsubstituted aryl group is preferably the one having 6 to 10 carbon atoms, such as phenyl group and naphthyl group.

Though there is no particular limitation, the unsubstituted heteroaryl group is preferably the one containing oxygen atom, sulfur atom or nitrogen atom as a hetero atom, and having 4 to 12 atoms for forming a ring. Preferred examples of the unsubstituted heteroaryl group include thienyl group, furyl group, pyrrolinyl group, pyridyl group, benzothienyl group, benzofuranyl group and benzopyrrolinyl group.

As the substituent (group substituted for 1 or 2 or more hydrogen atoms of the unsubstituted aryl group or of the unsubstituted heteroaryl group) possessed by the substituted aryl group and the substituted heteroaryl group, there can be exemplified those which are the same as those exemplified for the substituent (Rsb).

As the halogen atom, there can be exemplified a fluorine atom, a chlorine atom, a bromine atom or an iodine atom.

As the halogenoalkyl group, there can be exemplified the above-mentioned alkyl groups of which 1 or 2 or more hydrogen atoms are substituted by fluorine atoms, chlorine atoms or bromine atoms. Preferred examples of the halogenoalkyl group include fluoromethyl group, difluoromethyl group and trifluoromethyl group.

As the halogenoalkoxy group, there can be exemplified the above-mentioned alkoxy groups of which 1 or 2 or more hydrogen atoms are substituted with fluorine atoms, chlorine atoms or bromine atoms. Particularly preferred examples of the halogenoalkoxy group include fluoromethoxy group, difluoromethoxy group and trifluoromethoxy group.

The heterocyclic group which is the substitutent (Rsb) has a nitrogen atom as a hetero atom, and is bonded to the ring of the above-mentioned aromatic hydrocarbon group or of the aromatic heterocyclic group through the nitrogen atom, or is a condensed heterocyclic group that is formed as the heterocyclic group is further condensed with an aromatic hydrocarbon ring or an aromatic heterocyclic ring. It is desired that the number of carbon atoms constituting the heterocyclic ring as the substituent (Rsb) is, usually, 2 to 10 and, particularly, 2 to 6. The heterocyclic ring which is the substituent (Rsb) may further include hetero atoms such as oxygen atoms, sulfur atoms or nitrogen atoms in addition to nitrogen atoms bonded to the ring of the aromatic hydrocarbon group or of the aromatic heterocyclic group. The heterocyclic ring as the substituent (Rsb) may further have a substituent (here, the substituent may be the same as those exemplified for the substituent (Rsb)).

Preferred examples of the heterocyclic group which serves as the above-mentioned substituent (Rsb) include morpholino group, piperidino group, pyrrolydinyl group, piperadino group and indolinyl group.

In the group represented by above-mentioned formula (6), —W[(C$_2$H$_4$O)$_x$(C$_3$H$_6$O)$_y$(C$_4$H$_8$O)$_z$]$_a$—V, it is desired that W is —CH$_2$O—, —OC(=O)— or an oxygen atom and is, most desirably, an oxygen atom among those described above from the standpoint of photochromic properties and easy synthesis. From the standpoint of favorable compatibility to a high-molecular solid matrix, further, it is desired that V is a (meth)acryloyl group. As the alkyl group R$^a$ having 1 to 20 carbon atoms, there can be exemplified a methyl group, an ethyl group, a t-butyl group, a t-octyl group, a decyl group and a stearyl group. Among them, it is particularly desired to use the one having 1 to 6 carbon atoms.

In the formula (6), it is desired that x, y and z are integers of 0 to 20, and that the total number of x, y and z is 1 to 20.

Concerning the group V in the formula (6), there is no particular limitation on a group having an epoxy group with 1 to 5 carbon atoms. Preferably, however, there are exemplified an epoxy group and a glycidyl group and, particularly, a glycidyl group. As a group having a carboxyl group with 1 to 5 carbon atoms, there can be preferably exemplified an alkyl group having a carboxyl group, such as —CH$_2$CO$_2$H and —CH(CH$_3$)CO$_2$H, as well as —C(=O)(CH$_2$)CO$_2$H. As the aminoalkyl group having 1 to 6 carbon atoms, there can be exemplified 2-aminoethyl group and 2-aminobutyl group.

In the group represented by the above-mentioned formula (7), —W[(C$_2$H$_4$O)$_{x'}$(C$_3$H$_6$O)$_{y'}$(C$_4$H$_8$O)$_{z'}$]$_b$-T-[(C$_2$H$_4$O)$_{x''}$(C$_3$H$_6$O)$_{y''}$(C$_4$H$_8$O)$_{z''}$]$_c$—V, the divalent organic residue (containing a cyclic group and having 5 to 20 carbon atoms) denoted by T is typically a hydrocarbon group. Not being limited thereto only, however, the divalent organic residue T may be a group containing such a bond as ester bond, ether bond, amide bond, thioether bond, sulfonyl bond or urethane bond other than carbon-carbon bond. The cyclic group contained in the organic residue may be any one of aliphtatic hydrocarbon ring, heterocyclic ring or aromatic hydrocarbon ring, and the aliphatic hydrocarbon ring and the heterocyclic ring may be those of the crosslinked type. These rings may be 4- to 8-membered rings, or may be those formed by the condensation of 2 to 4 of these rings.

In the present invention, it is desired that the organic residue contains the above-mentioned rings in a plural number and, desirably, in a number of 2 to 4. Concrete examples of the organic residue include those which contain a benzene ring, a cyclohexane ring or an adamantane ring as represented by the following formulas,

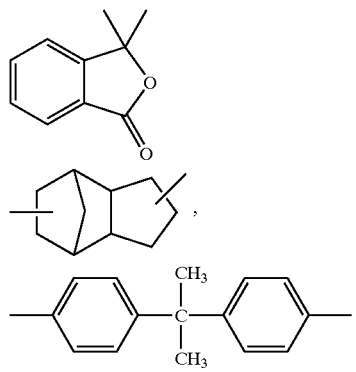

In the present invention, an organic residue represented by

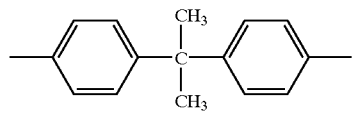

is most desired from the standpoint of obtaining more favorable photochromic properties.

In the present invention, further, the above-mentioned substituent (Rsb) is, particularly preferably, a alkyl group; alkoxy group; aralkyl group; amino group; substituted amino group; halogen atom; halogenoalkyl group; or substituted or unsubstituted heterocyclic group having nitrogen atom as a hetero atom, and is bonded via the nitrogen atom.

There is no particular limitation on the positions to where the above substituents (Rsb) are bonded and on the total number thereof.

In the present invention, when the trivalent group represented by the above-mentioned formula (2) or (3) is the one derived from a benzene ring that is described below, it is desired that the alkoxy group is bonded to the fifth position thereof or a nitrogen atom (hetero atom) of the substituted or unsubstituted heterocyclic group is bonded to the fifth position thereof from the standpoint of improving the color density.

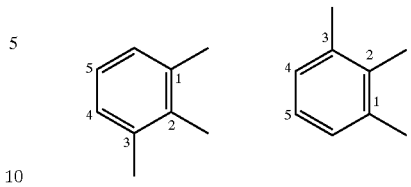

Divalent group Z.

In the above general formula (1), the divalent group Z (-Z-) is represented by the following formula (4) or (5),

 (4)

 (5)

In the above formulas (4) and (5), the groups represented by $R^7$, $R^8$ and $R^9$ are, independently from each other, alkylene groups, the groups represented by B and B' are, independently from each other, imino groups, substituted imino groups, oxy groups, thio groups, carbonyl groups, cycloalkylene groups, cycloalkylidene groups, or substituted or unsubstituted arylene groups, and m, n, p and q are 0 or 1.

Though there is no particular limitation, the alkylene groups represented by $R^7$ to $R^9$ are, desirably, those having 1 to 6 carbon atoms. Preferred examples of the alkylene group include straight-chain or branched-chain groups, such as methylene group, ethylene group, trimethylene group, tetramethylene group, propylene group, tetramethylethylene group and isopropylidene group.

The substituted imino groups represented B and B' are the ones represented by —NR'—, wherein the group R' may be the one that complies with the substituent (Rsb). Particularly preferred group R' may be an alkyl group with 1 to 6 carbon atoms, such as methyl group, ethyl group or propyl group, or a benzyl group.

As the cycloalkylene groups represented by B and B', there can be exemplified those having 3 to 20 carbon atoms and, preferably, 4 to 12 carbon atoms, such as cyclopropylene group, cyclobutylene group, cyclopentylene group, cyclohexylene group, cycloheptylene group, cyclooctylene group, cyclononylene group and cyclodecylene group.

As the cycloalkylidene groups represented by B and B', there can be exemplified those having 4 to 20 carbon atoms and, preferably, 4 to 12 carbon atoms, such as cyclobutylidene group, cyclopentylidene group, cyclohexylidene group, cycloheptylidene group, cyclooctylidene group and cyclononylidene group.

As the unsubstituted arylene groups represented by B and B', there can be exemplified those having 6 to 18 carbon atoms. Concrete examples of the arylene group include phenylene group, naphthylene group and phenanthrylene group.

As the substituted arylene groups represented by B and B', there can be exemplified those in which 1 or 2 or more hydrogen atoms in the unsubstituted arylene group are substituted by the alkyl group, alkoxy group, aralkyl group, aralkoxy group, amino group, substituted amino group, cycano group or nitro group, which are the same as those descirbed with reference to the above-mentioned substituent (Rsb).

In the present invention, the above-mentioned divalent group Z exhibits the effect of increasing the fading rate and to develop a color tone of a neutral tint. From the degree of effect and easy synthesis, here, it is desired that the groups B and b' are oxy groups, imino groups, substituted imino groups, cycloalkylene groups, cycloalkylidene groups, or substituted or unsubstituted arylene groups. Groups $R^1$ to $R^4$.

In the above general formula (1), the groups $R^1$, $R^2$, $R^3$ and $R^4$ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups or halogenoalkoxy groups. Among these groups, those that overlap on the groups described as the above substituents (Rsb) are the same as such groups.

Further, $R^1$ and $R^2$ together or $R^3$ and $R^4$ together may form a ring, and either $R^1$ or $R^2$ and either $R^3$ or $R^4$ together may form a ring. The thus formed ring may be either an aliphatic hydrocarbon ring or a heterocyclic ring, but is, more preferably, the aliphatic hydrocarbon ring. Further, these rings may have a substituent, and the number of atoms forming the ring is, desirably, from 3 to 20.

As the aliphatic hydrocarbon ring, there can be exemplified monocyclic rings having 3 to 20 carbon atoms, such as cyclopropane ring, cyclobutane ring, cyclopentane ring, cyclohexane ring, cycloheptane ring, cyclooctane ring, cyclononane ring, cyclodecane ring, cycloundecane ring, cyclododecane ring, cyclotridecane ring and cyclopentadodecane ring, or crosslinked aliphatic rings having 6 to 20 carbon atoms, such as bicyclo[2,2,1]heptane ring, bicyclo[2,2,2]octane ring, bicyclo[3,2,0]heptane ring, bicyclo[3,1,1]heptane ring, bicyclo[3,2,1]octane ring and adamantane ring. In the crosslinked aliphatic ring, there is no particular limitation on the positions of the bonding hands. Further, the aliphatic hydrocarbon ring may have a substituent which may be an alkyl group, a cycloalkyl group, an alkoxy group, an amino group or a substituted amino group described above as the substituent (Rsb). There is no particular limitation on the positions and the number of the substituents.

As the heterocyclic group, there can be exemplified oxygen-containing rings such as tetrahydrofurane ring and pyran ring; nitrogen-containing rings such as pyrrolidine ring, piperidine ring, morpholine ring, thiomorpholine ring, piperadine ring and hexamethyleneimine ring; carbonyl-containing rings such as cyclopentanone ring and cyclohexanone ring; ester-containing rings or oxygen-containing carbonyl mixed rings, such as butylolactone ring, tetrahydrofuranon ring and tetrahydropyranon ring; amide-containing rings or nitrogen-containing carbonyl mixed spiro rings, such as pyrrolidinone ring, piperidinone ring and oxohexamethyleneimine rings; and crosslinked rings, such as aza-bicyclo[2,2,2]octane ring, decahydro-cyclopentaazepine ring, aza-bicyclo[3,2,1]octane ring, octahydro-quinolizine ring, decahydro-pyridinoquinoline ring and aza-tricycloundecane ring.

As the substituent of the heterocyclic ring, there can be exemplified alkyl group, cycloalkyl group, alkoxy group, amino group, and substituted amino group that were exemplified above as the substituents (Rsb), and there is no limitation on the positions where the substituents are substituted or on the total number of the substituents.

When either $R^1$ or $R^2$ forms a ring together with either $R^3$ or $R^4$, it is desired that the substituent is a crosslinked aliphatic hydrocarbon ring having 7 to 18 carbon atoms among the above-mentioned rings, such as bicyclo[2,2,1]heptane ring, bicyclo[2,2,2]octane ring, bicyclo[3,2,1]octane ring, bicyclo[3,3,1]nonane ring or adamantane ring, or a crosslinked heterocyclic ring having 6 to 18 carbon atoms for forming a ring, such as aza-bicyclo[2,2,2]octane ring, decahydro-cyclopentaazepine ring, or aza-bicyclo[3,2,1]octane ring.

The ring formed by either $R^1$ or $R^2$ and by either $R^3$ or $R^1$ may be an aromatic hydrocarbon ring such as fluorene ring or phenanthrene ring.

In the present invention, a particularly preferred embodiment is that $R^1$ to $R^4$ are hydrogen atoms, alkyl groups, alkoxy groups or halogenoalkyl groups, $R^1$ and $R^2$ together and/or $R^3$ and $R^4$ together are forming rings, or either $R^1$ or $R^2$ and either $R^3$ or $R^4$ together are forming a ring. Among them, the effect of quick fading rate is particularly favorably exhibited when a ring is formed by $R^1$ to $R^4$, which is more desirable. In this case, the effect of the present invention is exhibited most distinctly when the ring is formed by the atoms of a number of 5 to 12.

Groups $R^5$ and $R^6$.

In the above-mentioned general formula (1), $R^5$ and $R^6$ are, independently from each other, alkyl groups, substituted or unsubstituted aryl groups, or substituted or unsubstituted heteroaryl groups. Here, $R^5$ and $R^6$ together may form a ring.

Here, the alkyl group, substituted or unsubstituted aryl group, or substituted or unsubstituted heteroaryl group are the same as those groups described as the substituents (Rsb).

Like the ring formed by $R^1$ to R mentioned above, the ring formed by $R^5$ and $R^6$ may be any one of aliphatic hydrocarbon ring, heterocyclic ring or aromatic hydrocarbon ring. Preferred examples of the aliphatic hydrocarbon ring include crosslinked rings having 6 to 18 carbon atoms, such as bicyclo[2,2,1]heptane ring, bicyclo[2,2,2]octane ring, bicyclo[3,2,1]octane ring and bicyclo[3.3.1]nonane ring. Preferred examples of the heterocyclic ring include crosslinked rings having 6 to 18 carbon atoms, such as aza-bicyclo[2,2,2]octane ring, decahydro-cyclopentaazepine ring, and aza-bicyclo[3,2,1]octane ring, and preferred examples of the aromatic hydrocarbon ring include those having 10 to 18 carbon atoms, such as fluorene ring and phenanthrene ring.

Further, the ring formed by $R^5$ and $R^6$, too, may have a substituent which may be alkyl group, alkoxy group, aryl group, hydroxyl group or halogen atom like the ones described concerning the substituent (Rsb).

In the present invention, it is particularly desired that at least either $R^5$ or $R^6$ is any one of the groups (i) to (iv) described below.

(i) An unsubstituted aryl group.
(ii) A substituted aryl group having, as a substituent, substituted amino group, alkyl group, cycloalkyl group or alkoxy group.
(iii) A substituted aryl group in which the substituent is a heterocyclic group having a nitrogen as a hetero atom and is bonded to the aryl group via the nitrogen atom (this heterocyclic group may further have a substituent).
(iv) The same substituted aryl group as that of
(iii) above in which a heterocyclic group which is the substituent is forming a condensed heterocyclic group being condenssed with the aromatic hydrocarbon ring or the aromatic heterocyclic ring.

In the substituted aryl groups of (ii) to (iv) described above, there is no particular limitation on the positions of the substituents bonded to the aryl group or on the total number of the substitutents. When the aryl group is a phenyl group, however, it is desired that the position of the substituent is the third position or the fourth position, and the number of the substituents is 1 or 2. Concrete examples of the preferred substituted phenyl group include 4-(N,N-dimethyllamino)

phenyl group, 4-(N,N,-diethylamino)phenyl group, 4-(N,N-diphenylamino)phenyl group, 4-morpholinophenyl group, 4-piperidinophenyl group, 4-methoxyphenyl group, 4-ethoxyphenyl group, 4-propoxyphenyl group, 4-butoxyphenyl group, 4-cyclohexylphenyl group, and 3,4-dimethoxyphenyl group. When the aryl group is the one other than the phenylgroup, it is desired that the number of the substituent is 1. Preferred examples of the substituted aryl group include 4-(N,N-dimethylamino)thienyl group, 4-(N,N-diethylamino)furyl group, 4-(N,N-diphenylamino) thienyl group, 4-morpholinopyrrolinyl group, 6-piperidinobenzothienyl group, and 6-(N,N-dimethylamino)benzofuranyl group. Chromene compounds.

The compound of the present invention expressed by the above-mentioned general formula (1) usually exists as a colorless sold at normal temperature and under normal pressure, and can be confirmed by the following means ① to ③.

① Measurement of a proton nuclear magnetic resonance spectrum ($^1$H-NMR) indicates peaks based on an aromatic proton and an alkene proton near $\delta 5.9$ to $9.0$ ppm and peaks based on an alkyl group and an alkylene group near $\delta 1.0$ to $4.0$ ppm. Upon relatively comparing the spectrum intensities at these peaks, further, the numbers of protons in the bonding groups can be known.

② The compositions of the corresponding products can be determined by the elemental analysis.

③ Measurement of a $^{13}$C-nuclear magnetic resonance spectrum ($^{13}$C-NMR) indicates a peak based on a carbon atom of an aromatic hydrocarbon group near $\delta 110$ to $160$ ppm, a peak based on a carbon atom of alkene near $\delta 80$ to $140$ ppm, and peaks based on carbon atoms of an alkyl group and an alkylene group near $\delta 20$ to $80$ ppm.

The chromene compound of the present invention represented by the above-mentioned general formula (1) exhibits excellent photochromic properties such as small initial color, large fading rate, excellent light resistance while developing a color tone of a neutral tint. Among the chromene compounds of the present invention, the most excellent photochromic characteristics are exhibited by the following compounds.

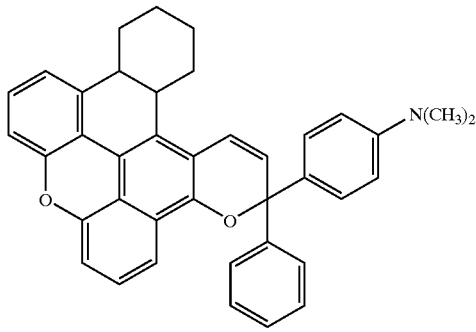

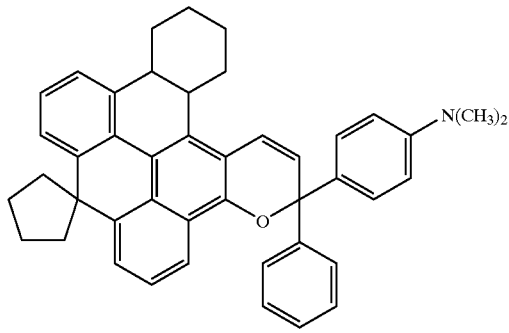

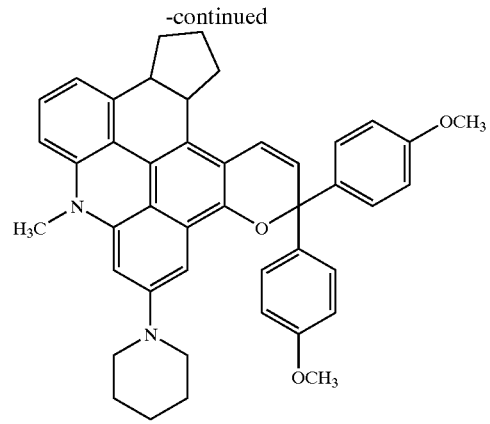

Though there is no particular limitation, the chromene compound of the present invention can be produced by, for example, a method described below (in the general formulas (8) and (9) representing a naphthol derivative and a propargyl alcohol used in the following production process, the groups $R^1$ to $R^6$, rings X and Y, and the divalent group Z are as defined in the general formula (1)).

Namely, a chromene compound represented by the above general formula (1) is obtained by reacting a naphthol derivative represented by the following general formula (8), (8)

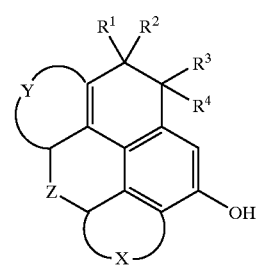

with a propargyl alcohol derivative represented by the following general formula (9), (9)

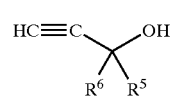

in the presence of an acid catalyst.

In the reaction in the presence of the acid catalyst, though there is no particular limitation, the naphthol derivative and the propargyl alcohol derivative are usually used at a ratio satisfying molar ratios of 1:10 to 10:1.

As the acid catalyst, further, there is used sulfuric acid, benzenesulfonic acid, p-toluenebenzenesulfonic acid or acidic alumina in an amount of from 0.1 to 10 parts by weight per the toal amount of 100 parts by weight of the naphthol derivative and the propargyl alcohol derivative.

The reaction temperature is usually 0 to 200° C., and the solvent is a non-protonic organic solvent, such as N-methylpyrrolidone, dimethylformamide, tetrahydrofurane, benzene or toluene.

The chromene compound of the present invention obtained through the above reaction dissolves well in a general organic solvent such as toluene, chloroform or tetrahydrofurane. A solution obtained by dissolving the chromene compound in the above solvent is, usually, colorless and transparent, and exhibits a favorable reversible photochromic action quickly developing a color when it is irradiated with sunlight or ultraviolet rays and quickly returning to the initial colorless state when it is shut off the light.

The above photochromic action of the chromene compound of the present invention is similarly exhibited even in a high-molecular solid matrix. The high-molecular solid matrix may be the one in which the chromene compound of the present invention disperses homogeneously. Optically preferred examples include such thermoplastic resins as polymethylacrylate, polyethylacrylate, polymethylmethacrylate, polyethylmethacrylate, polystyrene, polyacrylonitrile, polyvinyl alcohol, polyacrylamide, poly(2-hydroxyethyl methacrylate), polydimethylsiloxane, polyethylene glycol monoallyl ether, and polycarbonate.

A curable resin obtained by polymerizing a radically polymerizable polyfunctional monomer, too, can be used as a high-molecular solid matrix. In the above curable resin, examples of the radically polymerizable polyfunctional monomer include polyvalent acrylic acid and polyvalent methacrylic acid ester compounds, such as ethylene glycol diacrylate, ethylene glycol dimethacrylate, diethylene glycol dimethacrylate, triethylene glycol dimethacrylate, tetraethylene glycolate dimethacrylate, ethylene glycol bisglycidyl methacrylate, polyethylene glycol diacrylate, urethane oligomer hexaacrylate, bisphenol A dimethacrylate, trimethylolpropane trimethacrylate, 2,2-bis(4-methacryloyloxyethoxyphenyl)propane, and 2,2-bis(3,5-dibromo-4-methacryloyloxyethoxyphenyl)propane; polyvalent allyl compounds, such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, allyl diglycol carbonate and trimethylolpropanetriallyl carbonate; polyvalent thioacrylic acid and polyvalent thiomethacrylic acid ester compounds, such as 1,2-bis(methacryloylthio)ethane, bis(2-acryloylthioethyl)ether, and 1,4-bis(methacryloylthiomethyl)benzene; acrylic acid ester compounds and methacrylic acid ester compounds, such as glycidyl acrylate, glycidyl methacrylate, γ-methacryloyloxypropyltrimethoxy silane, β-methylglycidyl methacrylate, bisphenol A monoglycidyl ether methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, and 3-glycidyloxy-2-hydroxypropyloxy)-2-hydroxypropyl acrylate; and divinyl benzene.

A copolymer of the above radically polymerizable polyfunctional monomer and a monofunctional radical polymer, too, can be used as a high-molecular solid matrix. As the monofunctional radical polymer, there can be exemplified unsaturated carboxylic acid, such as acrylic acid, methacrylic acid and maleic anhydride; acrylic acid and methacrylic acid ester compounds, such as methyl acrylate, methyl methacrylate, benzyl methacrylate, phenyl methacrylate and 2-hydroxyethyl methacrylate; fumaric acid ester compounds such as diethyl fumarate and diphenyl fumarate; thioacrylic acid and thiomethacrylic acid ester compounds, such as methyl thioacrylate, benzyl thioacrylate and benzyl thiomethacrylate; and vinyl compounds, such as styrene, chlorostyrene, methylstyrene, vinylnaphthalene, α-methylstyrene dimer and bromostyrene.

When the above-mentioned radically polymerizable monomer is to be polymerized by the irradiation with ultraviolet rays, there is preferably used, as a photopolymerization initiator, benzoin, benzoinmethyl ether, benzoinbutyl ether, benzophenol, acetophenone 4,4'-dichlorobenzophenone, diethoxyacetophenone, 2-hydroxy-2-methyl-1-phenylpropane-1-on, benzylmethylketal, 1-(4-isopropylphenyl)-2-hydroxy-2-methylpropane-1-on, 1-hydroxycyclohexylphenyl ketone, 2-isopropylthioxanthone, bis(2,6-dimethoxybenzoyl-2,4,4-trimethyl-pentyl phosphineoxide, bis(2,4-6-trimethylbenzoyl)-phenyl phosphineoxide, 2,4,6-trimethylbenzoyldiphenyl phosphineoxide, and 2-benzyl-2-dimethylamino-1-(4-morpholinophenyl)-butanone-1.

There is no particular limitation on the method of dispersing the chromene compound of the present invention in the above-mentioned high-molecular solid matrix, and there can be used a generally employed method. For example, there can be exemplified a method of kneading the thermoplastic resin and the chromene compound together in a molten state to disperse the chromene compound in the resin, a method of dissolving a chromene compound in the polymerizable monomer, adding a polymerization catalyst thereto, and effecting the polymerization with heat or light to disperse the chromene compound in the resin, or a method of dyeing the surfaces of the thermoplastic resin and of the curable resin with a chromene compound, so that the chromene compound disperses in the resin.

The chromene compound of the present invention can be used as a photochromic material over a wide range, such as various memory materials to substitute for silver salt photosensitive materials, i.e., can be used as a copying material, a photosensitive material for printing, a memory material for cathode-ray tubes, a photosensitive material for lasers and as a photosensitive material for holography. Further, the photochromic material using the chromene compound of the present invention can be utilized as a photochromic lens material, an optical filter material, a display material, an actinometer and as an ornamental material.

For photochromic lenses, for example, the chromene compound of the present invention can be used by any method so far as there is obtained a homogeneous dimming property. Concretely speaking, the chromene compound of the present invention is used by a variety of methods such as a method by which a polymer film in which the chromene compound of the present invention is homogeneously dispersed, is sandwiched in the lens or is laminated thereon; a method by which the chromene compound of the invention is dispersed in the polymerizable monomer and is polymerized according to a predetermined method to obtain a photochromic lens; a method by which the chromene compound of the present invention is dispersed in the polymerizable monomer to prepare a photochromic monomer composition, and the monomer composition is applied to the surfaces of a non-photochromic lens material to obtain a lens on which a photochromic film is laminated; a method by which the chromene compound of the present invention is dissolved in, for example, a silicone oil, and the lens surfaces are impregnated with the chromene compound at 150 to 200° C. over a period of 10 to 60 minutes and, then, the surfaces thereof are coated with a curable material to obtain a photochromic lens; or a method by which a polymer film in which the chromene compound of the invention has been homogeneously dispersed is formed on the surface of the lens which is, then, coated with a curable material to obtain a photochromic lens.

The chromene compound of the present invention exhibits a high fading rate in a solution or in a high-molecular solid matrix. Besides, in a state of not being irradiated with light, the chromene compound of the invention exhibits little color. Even after used for extended periods of time, the chromene compound of the invention exhibits little color yet maintaining good photochromic property. For example, the photochromic lens using the chromene compound of the present invention quickly resumes its initial color tone when it is brought indoors from outdoors and, further exhibits little color even after used for extended periods of time, thus featuring good light resistance.

When placed in a state of developing color, further, the chromene compound of the present invention exhibits two absorption bands of from 420 to 520 nm and from 520 to 620 nm, producing a small difference in the intensity of absorption between the two bands and a ratio of color densities of usually in a range of from 0.7 to 1.5. It is, therefore, possible to develop a color tone of a neutral tint such as grey or brown even by using a single compound.

EXAMPLES

The present invention will be described in further detail by way of Examples to which only, however, the invention is in no way limited.

Example 1

6.3 Grams (0.02 mols) of a naphthol derivative of the following formula,

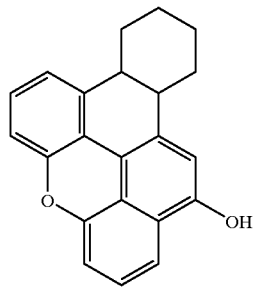

and 5.5 g (0.022 mols) of a propargyl alcohol derivative of the following formula,

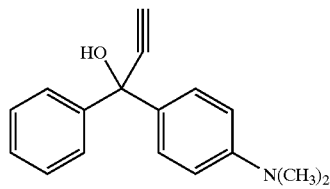

were dissolved in 50 ml of toluene, followed by the addition of 0.05 g of a p-toluenesulfonic acid, and the mixture was stirred at a refluxing temperature for one hour. After the reaction, the solvent was distilled off, and the reaction product was refined by a chromatography on silica gel to obtain 3.1 g of a pale bluish powdery product, yield, 28%.

The values of elemental analysis of the product were:

C: 85.44%
H: 6.02%
N: 2.57%
O: 5.97% which were in very good agreement with the calculated values (C: 85.53%, H: 6.07%, N: 2.56%, O: 5.84%) of $C_{29}H_{33}NO_2$.

Measurement of the proton nuclear magnetic resonance spectrum indicated a peak of 16 H based on an alkylene group near δ1.0 to 4.0 ppm, and peaks of 17H based on an aromatic proton and on an alkene proton near δ5.6 to 9.0 ppm.

Further, measurement of a 13C-nuclear magnetic resonance spectrum indicated a peak based on a carbon atom of an aromatic ring near δ110 to 160 ppm, a peak based on a carbon atom of an alkene near δ80 to 140 ppm, and a peak based on a carbon atom of an alkyl at δ20 to 60 ppm.

From the above results, it was confirmed that the isolated product was a compound represented by the following structural formula. FIG. 1 shows a $^1$H-NMR spectrum of the compound that was obtained.

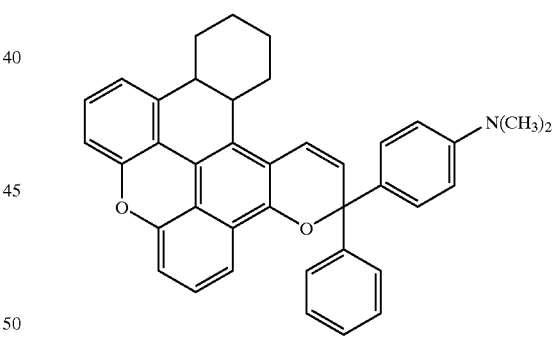

Examples 2 to 22

Chromene compounds shown in Tables 1 to 6 were synthesized in the same manner as in Example 1. The obtained products were analyzed for their structures by using the same structure confirmation means as that of Example 1 to make sure that the compounds possessed the structures represented by the structural formulas shown in Tables 1 to 6. Tables 7 and 8 show values of elemental analyses of these compounds as well as values found from the structural formulas of these compounds.

TABLE 1
| | Starting material | |
|---|---|---|
| Ex. No. | Naphthol derivative | Propargyl alcohol |
| 2 | 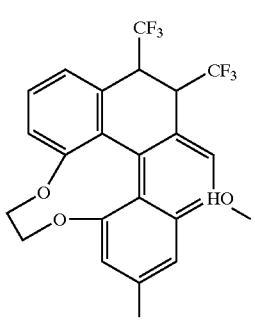 | 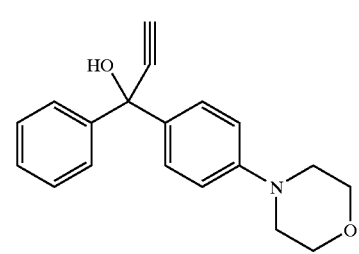 |
| 3 | 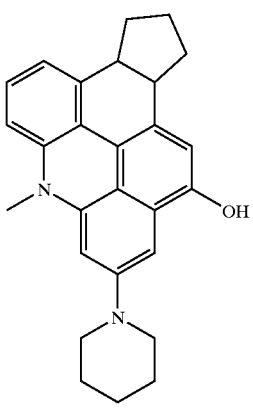 | 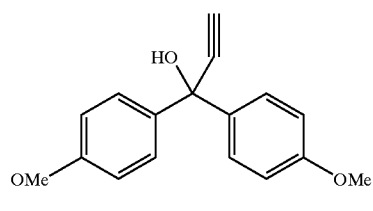 |
| 4 | 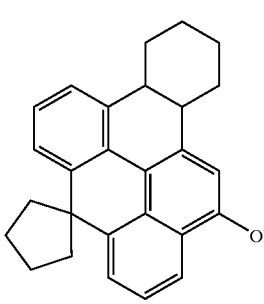 | 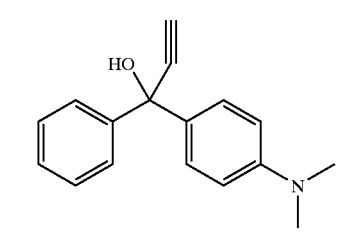 |
| 5 | 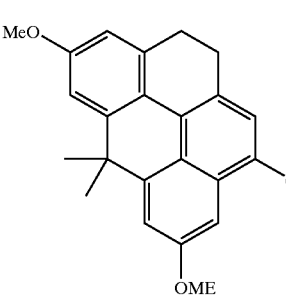 | 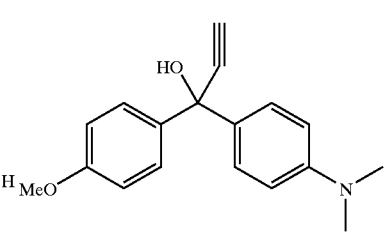 |

TABLE 1-continued

| Ex. No. | Product | Yield (%) |
| --- | --- | --- |
| 2 | | 21 |
| 3 | | 16 |
| 4 | | 33 |
| 5 | | 27 |

TABLE 2

| Ex. No. | Starting material | |
| --- | --- | --- |
| | Naphthol derivative | Propargyl alcohol |
| 6 | | |
| 7 | | |
| 8 | | |
| 9 | | |

TABLE 2-continued

| Ex. No. | Product | Yield (%) |
|---|---|---|
| 6 | | 26 |
| 7 | | 22 |
| 8 | | 29 |
| 9 | | 27 |

TABLE 3

| Ex. No. | Starting material | |
|---|---|---|
| | Naphthol derivative | Propargyl alcohol |
| 10 | | |
| 11 | | |
| 12 | | |
| 13 | | |

TABLE 3-continued
| Ex. No. | Product | Yield (%) |
|---|---|---|
| 10 | 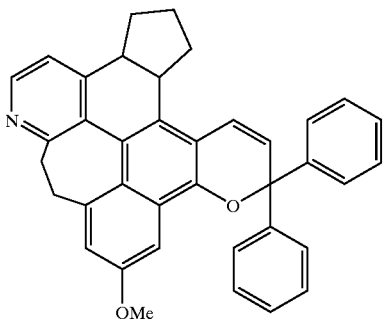 | 16 |
| 11 | 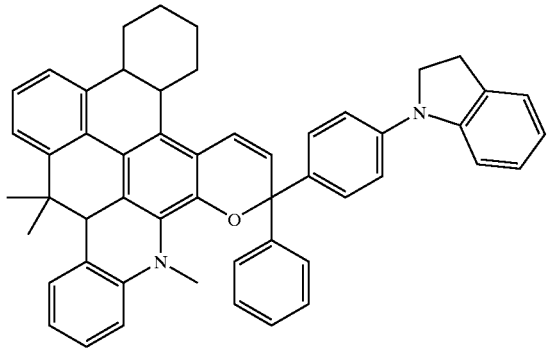 | 19 |
| 12 | 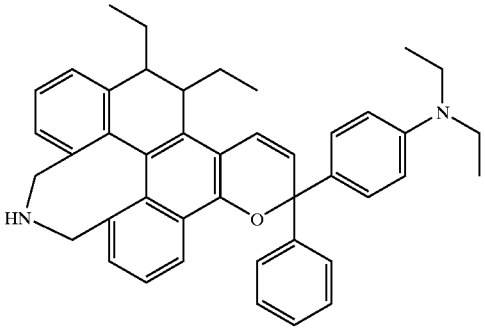 | 21 |
| 13 | 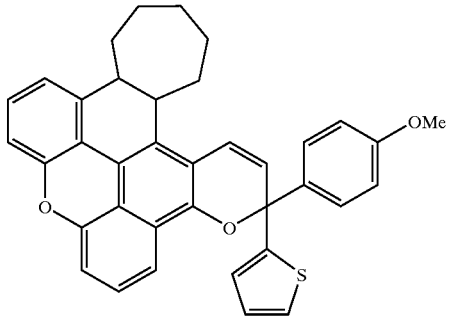 | 17 |

TABLE 4
| Ex. No. | Starting material | |
|---|---|---|
| | Naphthol derivative | Propargyl alcohol |
| 14 | 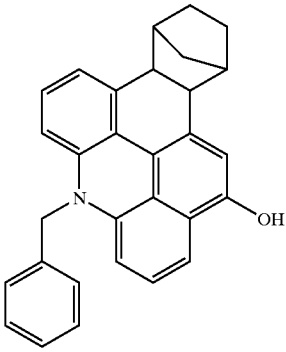 | 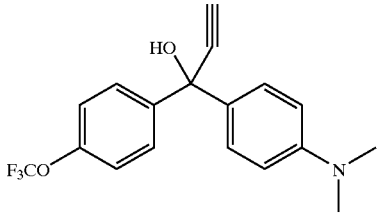 |
| 15 | 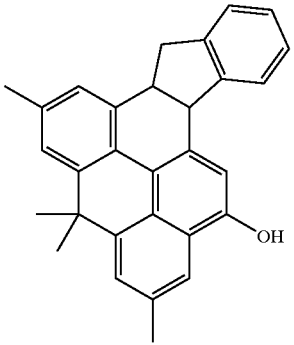 | 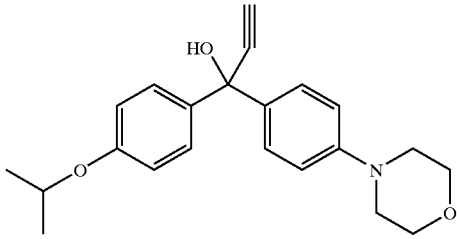 |
| 16 | 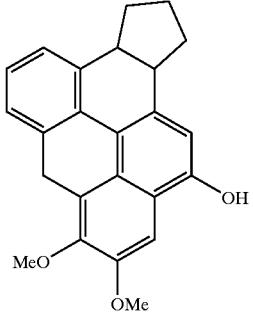 | 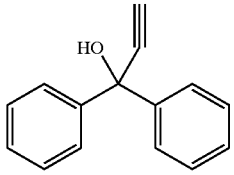 |
| 17 | 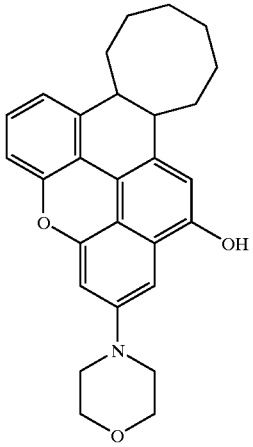 | 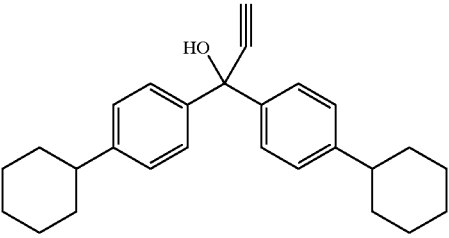 |

TABLE 4-continued
| Ex. No. | Product | Yield (%) |
|---|---|---|
| 14 | 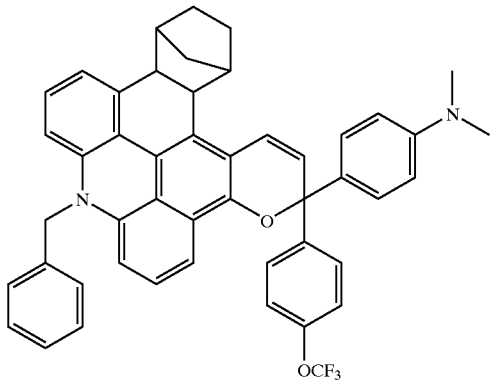 | 22 |
| 15 | 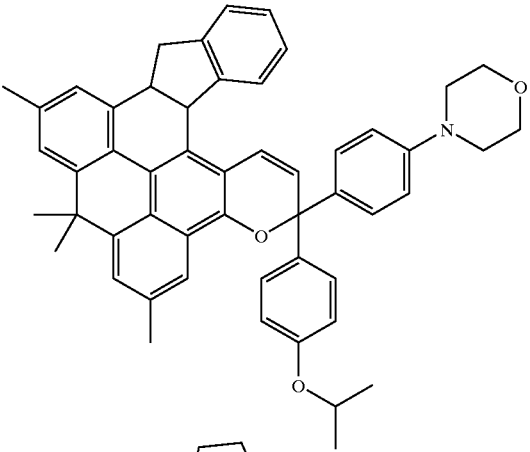 | 24 |
| 16 | 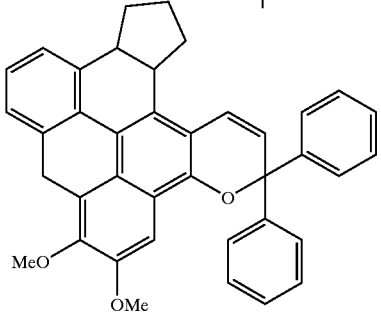 | 31 |
| 17 | 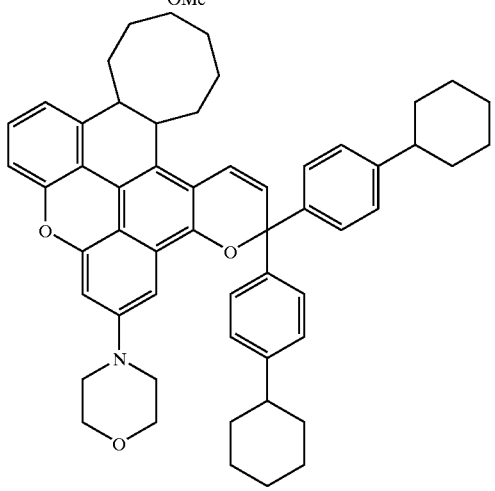 | 19 |

TABLE 5

| Ex. No. | Starting material | | 
| --- | --- | --- |
| | Naphthol derivative | Propargyl alcohol |
| 18 | | |
| 19 | | |
| 20 | | |

| Ex. No. | Product | Yield (%) |
| --- | --- | --- |
| 18 | | 22 |

TABLE 5-continued
| 19 | 21 |
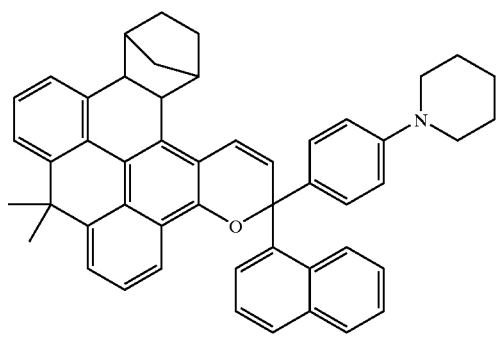
| 20 | 26 |
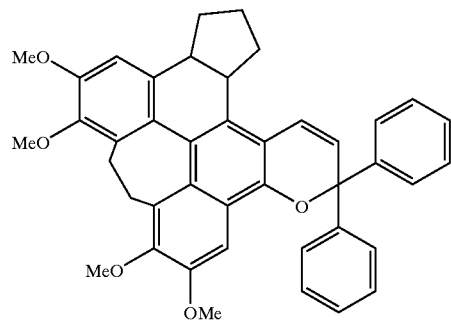
TABLE 6
| | Starting material | |
|---|---|---|
| Ex. No. | Naphtol derivative | Propargyl alcohol |
| 21 | | |
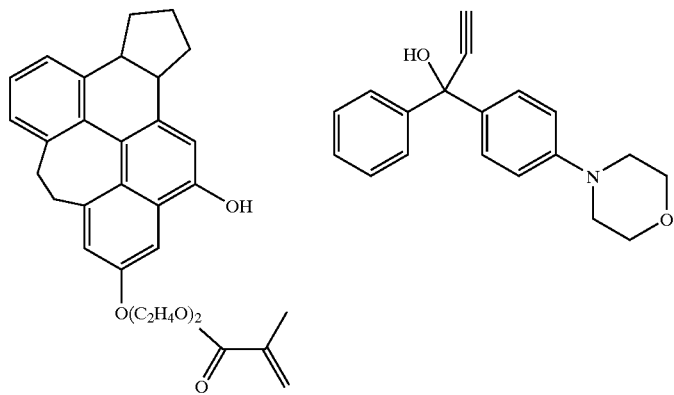

TABLE 6-continued
| | | |
|---|---|---|
| 22 | 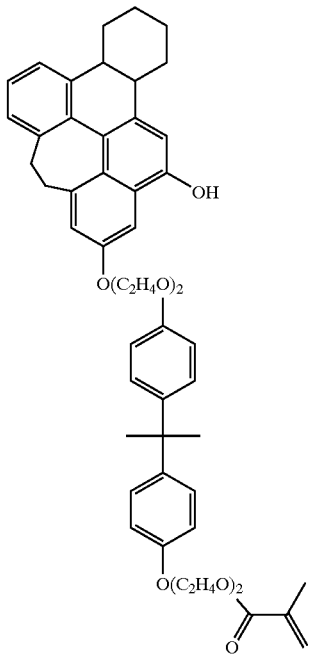 | 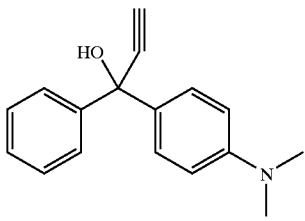 |
| Ex. No. | Product | Yield (%) |
|---|---|---|
| 21 | 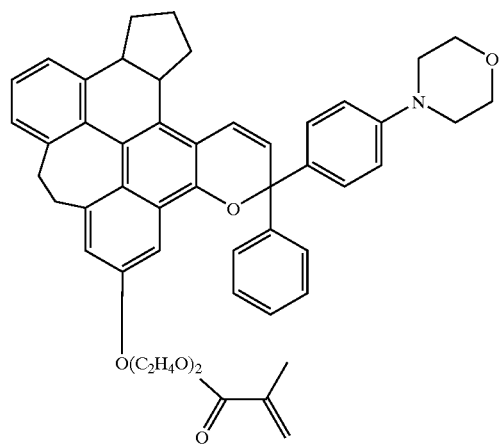 | 21 |
| 22 | 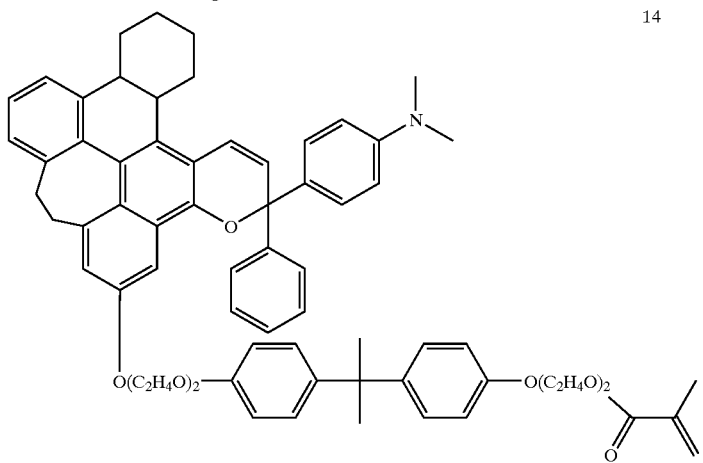 | 14 |

TABLE 7

| Ex. No. | Found C | H | N | O | Others | Calculated C | H | N | O | Others | ¹H-NMR (NMR) | |
|---|---|---|---|---|---|---|---|---|---|---|---|---|
| 2 | 67.62 | 4.48 | 1.91 | 10.72 | F: 15.27 | 67.65 | 4.46 | 1.88 | 10.73 | F: 15.29 | δ5.6~9.0<br>δ1.0~4.0 | 16H<br>17H |
| 3 | 81.7 | 6.58 | 4.31 | 7.41 | | 81.7 | 6.54 | 4.33 | 7.42 | | δ5.6~9.0<br>δ1.0~4.0 | 15H<br>27H |
| 4 | 88.13 | 6.91 | 2.31 | 2.65 | | 88.11 | 6.89 | 2.34 | 2.67 | | δ5.6~9.0<br>δ1.0~4.0 | 17H<br>24H |
| 5 | 80.77 | 6.45 | 2.29 | 10.49 | | 80.76 | 6.45 | 2.3 | 10.5 | | δ5.6~9.0<br>δ1.0~4.0 | 14H<br>25H |
| 6 | 88.95 | 6.12 | 2.28 | 2.65 | | 88.93 | 6.14 | 2.3 | 2.63 | | δ5.6~9.0<br>δ1.0~4.0 | 21H<br>16H |
| 7 | 83.28 | 6.46 | 2.32 | 7.94 | | 83.27 | 6.49 | 2.31 | 7.92 | | δ5.6~9.0<br>δ1.0~4.0 | 16H<br>23H |
| 8 | 81.67 | 6.55 | 2.12 | 9.67 | | 81.69 | 6.54 | 2.12 | 9.65 | | δ5.6~9.0<br>δ1.0~4.0 | 15H<br>28H |
| 9 | 85.38 | 6.09 | | 8.53 | | 85.39 | 6.08 | | 8.53 | | δ5.6~9.0<br>δ1.0~4.0 | 16H<br>18H |
| 10 | 85.52 | 5.86 | 2.62 | 6 | | 85.51 | 5.88 | 2.6 | 6.01 | | δ5.6~9.0<br>δ1.0~4.0 | 16H<br>15H |
| 11 | 87.36 | 6.49 | 3.92 | 2.24 | | 87.38 | 6.48 | 3.9 | 2.24 | | δ5.6~9.0<br>δ1.0~4.0 | 22H<br>24H |

TABLE 8

| Ex. No. | Found C | H | N | O | Others | Calculated C | H | N | O | Others | ¹H-NMR (NMR) | |
|---|---|---|---|---|---|---|---|---|---|---|---|---|
| 12 | 85.39 | 7.33 | 4.63 | 2.65 | | 85.38 | 7.33 | 4.61 | 2.68 | | δ5.6~9.0<br>δ1.0~4.0 | 17H<br>27H |
| 13 | 80.12 | 5.45 | | 8.65 | S: 5.78 | 80.12 | 5.44 | | 8.64 | S: 5.80 | δ5.6~9.0<br>δ1.0~4.0 | 15H<br>15H |
| 14 | 78.67 | 5.36 | 3.82 | 4.37 | F: 7.78 | 78.66 | 5.33 | 3.81 | 4.39 | F: 7.81 | δ5.6~9.0<br>δ1.0~4.0 | 21H<br>18H |
| 15 | 84.86 | 6.71 | 1.9 | 6.52 | | 84.89 | 6.69 | 1.91 | 6.51 | | δ5.6~9.0<br>δ1.0~4.0 | 18H<br>31H |
| 16 | 85.37 | 5.88 | | 8.75 | | 85.35 | 5.89 | | 8.76 | | δ5.6~9.0<br>δ1.0~4.0 | 16H<br>16H |
| 17 | 84.47 | 7.6 | 1.79 | 6.14 | | 84.49 | 7.59 | 1.78 | 6.14 | | δ5.6~9.0<br>δ1.0~4.0 | 15H<br>44H |
| 18 | 81.3 | 6.67 | | 12.03 | | 81.33 | 6.61 | | 12.06 | | δ5.6~9.0<br>δ1.0~4.0 | 14H<br>30H |
| 19 | 88.85 | 6.71 | 2.07 | 2.37 | | 88.88 | 6.72 | 2.04 | 2.36 | | δ5.6~9.0<br>δ1.0~4.0 | 19H<br>26H |
| 20 | 81 | 6.15 | | 12.85 | | 81.03 | 6.14 | | 12.83 | | δ5.6~9.0<br>δ1.0~4.0 | 16H<br>33H |
| 21 | 79.03 | 6.5 | 1.84 | 12.63 | | 79.05 | 6.51 | 1.84 | 12.6 | | δ5.6~9.0<br>δ1.0~4.0 | 14H<br>24H |
| 22 | 79.27 | 6.95 | 1.36 | 12.42 | | 79.16 | 6.99 | 1.34 | 12.51 | | δ5.6~9.0<br>δ1.0~4.0 | 24H<br>47H |

Applied Examples

Each of the chromene compounds obtained in Examples 1 to 22 in an amount of 0.04 parts by weight, were added to 13 parts by weight of a tetraethylene glycol dimethacrylate, 48 parts by weight of a 2,2-bis[4-(methacryloxyethoxy)phenyl]propane, 2 parts by weight of a polyethylene glycol monoallyl ether, 20 parts by weight of a trimethylolpropane trimethacrylate, and 9 parts by weight of a glycidyl methacrylate, and to which was further added, as a polymerization initiator, 1 part by weight of a t-butylperoxy 2-ethyl hexanate, and the mixture was mixed together to a sufficient degree.

The mixture was poured into a mold constituted by glass plates and a gasket of an ethylene/vinyl acetate copolymer, and was cast-polymerized. The polymerization was conducted by using an air furnace while gradually raising the temperature from 30° C. to 90° C. over 18 hours, and the temperature of 90° C. was maintained for 2 hours. After the polymerization, the polymer was taken out from the glass mold.

The obtained polymer (sample having a thickness of 2 mm) was irradiated with light by using a xenon lamp L-2480 (300W) SHL-100 manufactured by Hamamatsu Photonics Co. through an aeromass filter (manufactured by Coning Co.) at a temperature of 20±1° C. at beam intensities on the polymer surface of 2.4 mW/cm² (365 nm) and 24 μW/cm² (245 nm) for 120 seconds to develop color and to measure the photochromic properties of the sample. The photochromic properties were evaluated by the following methods, and were as shown in Tables 9 and 10.

① Maximum absorption wavelength ($\lambda$max): A maximum absorption wavelength after the development of color was found by using a spectrophotometer (instantaneous multi-channel photodetector MCPD 1000) manufactured by Otsuka Denshi Co. The maximum absorption wavelength is related to the color tone at the time when the color is developed.

② Color density {$\epsilon(120)-\epsilon(0)$}: A difference between an absorbancy $\epsilon(120)$ after irradiated with light for 120 seconds at a maximum absorption wavelength and $\epsilon(0)$ in a state of not irradiated with light. It can be said that the higher this value, the more excellent the photochromic properties are.

③ Fading rate {$\tau 1/2$ (min.)}: The time until the absorbency of a sample at a maximum wavelength drops down to one-half the {$\epsilon(120)-\epsilon(0)$} from when the sample is no longer irradiated with light after it was irradiated with light for 120 seconds. It can be said that the shorter the time, the more excellent the photochromic properties are.

④ Initial color (YI): The coloring degree was measured by using a color difference meter (SM-4) manufactured by Suga Shikenki Co. It can be said that the smaller the value YI, the smaller the coloring degree in a state of not being irradiated with light, which is excellent.

⑤ Remaining factor (%): The following deterioration promotion testing was conducted in order to evaluate the light resistance of color developed by the irradiation with light. That is, the obtained polymer (sample) was deteriorated by using a xenon weather meter X25 manufactured by Suga Shikenki Co. for 200 hours. Thereafter, the color densities were evaluated before and after the testing; i.e., a color density (A0) before the testing and a color density (A200) after the testing were measured, and a value {(A200/A0)×100} was calculated as a remaining factor (%) to use it as an index of resistance of the developed color. The higher the remaining factor, the higher the resistance of the developed color.

⑥ Ratio of color densities: A ratio of absorbancy at a maximum absorption wavelength was calculated in compliance with the formula [{$\epsilon 1(120)-\epsilon 1(0)$}/{$\epsilon 2(120)-\epsilon 2(0)$}]

where $\epsilon 1$ is an absorbancy at a maximum absorption wavelength on the side of the short wavelength, and $\epsilon 2$ is an absorbancy at a maximum absorption wavelength on the side of the long wavelength, and is used as an index of developing a color tone of a neutral tint. A favorable neutral tint is obtained as the density ratio approaches 1.

TABLE 9

| Ex. No. | λmax (nm) | Color density $\epsilon(120)-\epsilon(0)$ | Fading rate $\tau\frac{1}{2}$(min.) | Initial color YI | Remaining factor {A200/A0} × 100 | Color density ratio |
|---|---|---|---|---|---|---|
| 1 | 482 | 0.88 | 0.6 | 9 | 76 | 0.90 |
|   | 582 | 0.98 | 0.6 |   |   |   |
| 2 | 490 | 0.96 | 1.3 | 8 | 81 | 0.97 |
|   | 592 | 0.99 | 1.3 |   |   |   |
| 3 | 464 | 1.18 | 0.8 | 10 | 83 | 1.20 |
|   | 590 | 0.98 | 0.8 |   |   |   |
| 4 | 484 | 0.79 | 0.5 | 4 | 86 | 0.93 |
|   | 588 | 0.85 | 0.5 |   |   |   |
| 5 | 498 | 0.84 | 1.4 | 6 | 82 | 1.14 |
|   | 596 | 0.74 | 1.4 |   |   |   |
| 6 | 486 | 0.83 | 0.6 | 7 | 82 | 0.97 |
|   | 588 | 0.86 | 0.6 |   |   |   |
| 7 | 488 | 0.92 | 0.6 | 7 | 82 | 0.95 |
|   | 598 | 0.97 | 0.6 |   |   |   |
| 8 | 482 | 0.92 | 1.0 | 6 | 80 | 0.85 |
|   | 584 | 1.08 | 1.0 |   |   |   |
| 9 | 424 | 1.18 | 1.4 | 6 | 81 | 0.98 |
|   | 538 | 1.21 | 1.4 |   |   |   |
| 10 | 444 | 0.72 | 1.2 | 10 | 77 | 0.82 |
|   | 562 | 0.88 | 1.2 |   |   |   |
| 11 | 492 | 0.92 | 0.6 | 11 | 72 | 1.10 |
|   | 598 | 0.84 | 0.6 |   |   |   |

TABLE 10

| Ex. No. | λmax (nm) | Color density ε (120)−ε (0) | Fading rate τ½(min.) | Initial color YI | Remaining factor {A200/A0} × 100 | Color density ratio |
|---|---|---|---|---|---|---|
| 12 | 494 | 0.72 | 0.5 | 4 | 81 | 0.90 |
|  | 600 | 0.80 | 0.5 |  |  |  |
| 13 | 482 | 0.79 | 1.3 | 10 | 75 | 0.85 |
|  | 584 | 0.93 | 1.3 |  |  |  |
| 14 | 462 | 0.71 | 0.7 | 8 | 83 | 0.88 |
|  | 588 | 0.81 | 0.7 |  |  |  |
| 15 | 482 | 0.55 | 0.4 | 8 | 79 | 0.76 |
|  | 596 | 0.72 | 0.4 |  |  |  |
| 16 | 448 | 1.09 | 0.7 | 9 | 81 | 1.18 |
|  | 540 | 0.92 | 0.7 |  |  |  |
| 17 | 426 | 1.21 | 0.7 | 11 | 78 | 1.38 |
|  | 546 | 0.88 | 0.7 |  |  |  |
| 18 | 482 | 1.02 | 1.4 | 6 | 82 | 0.89 |
|  | 562 | 1.15 | 1.4 |  |  |  |
| 19 | 492 | 1.18 | 1.5 | 15 | 73 | 0.94 |
|  | 608 | 1.25 | 1.5 |  |  |  |
| 20 | 434 | 1.22 | 1.7 | 8 | 79 | 1.09 |
|  | 532 | 1.12 | 1.7 |  |  |  |
| 21 | 478 | 0.78 | 1.3 | 6 | 82 | 0.85 |
|  | 584 | 0.92 | 1.3 |  |  |  |
| 22 | 482 | 0.88 | 1.4 | 7 | 83 | 0.86 |
|  | 592 | 1.02 | 1.4 |  |  |  |

Comparative Examples 1 to 3

For comparison, photochromic polymers were obtained in the same manner as the above applied Examples but using the compounds represented by the following formulas (A), (B) and (C),

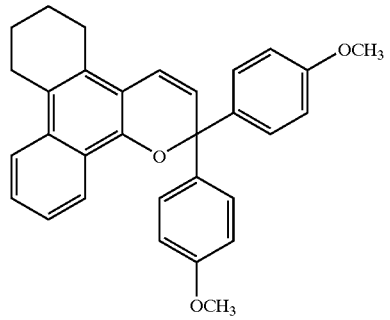

(A)

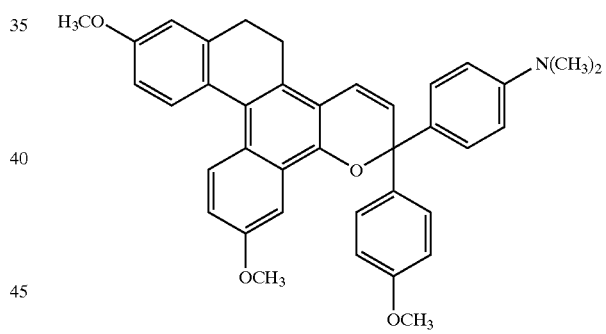

(B)

(C)

and their properties were evaluated. The results were as shown in Table 11.

TABLE 11

| Comp. Ex. No. | Compound No. | λmax (nm) | Color density ε(120)−ε(0) | Fading rate τ½(min.) | Coloring degree YI | Remaining factor {A200/A0} × 100 | Color density ratio |
|---|---|---|---|---|---|---|---|
| 1 | A | 522 | 0.86 | 8.3 | 3 | 68 | — |
| 2 | B | 498 | 0.92 | 4.1 | 4 | 71 | 1.10 |
|   |   | 596 | 0.84 | 4.1 |   |   |   |
| 3 | C | 484 | 0.45 | 1.3 | 14 | 77 | 0.50 |
|   |   | 610 | 0.90 | 1.3 |   |   |   |

Examples 1 to 22 using the chromene compounds of the present invention are superior in three effects, i.e., fading rate, initial color and color density ratio, to those of Comparative Examples 1 to 3.

What is claimed is:

1. A chromene compound represented by the following formula (1),

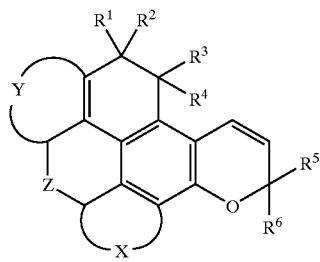

(1)

wherein $R^1$, $R^2$, $R^3$ and $R^4$ are, independently from each other, hydrogen atoms, hydroxyl groups, alkyl groups, alkoxy groups, aralkyl groups, aralkoxy groups, amino groups, substituted amino groups, cyano groups, nitro groups, halogen atoms, halogenoalkyl groups or halogenoalkoxy groups, $R^1$ and $R^2$ together, and $R^3$ and $R^4$ together, may form rings, and either $R^1$ or $R^2$ and either $R^3$ or $R^4$ together may form a ring, $R^5$ and $R^6$ are, independently from each other, alkyl groups, substituted or unsubstituted aryl groups, or substituted or unsubstituted heteroaryl groups, or $R^5$ and $R^6$ together may form a ring, a trivalent cyclic group represented by the following formula (2),

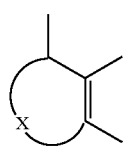

(2)

and a trivalent cyclic group represented by the following formula (3),

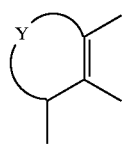

(3)

are, independently from each other, substituted or unsubstituted aromatic hydrocarbon groups or substituted or unsubstituted aromatic heterocyclic groups, and a divalent group Z is presented by the following formula (4) or (5),

(4)

(5)

wherein $R^7$, $R^8$ and $R^9$ are, independently from each other, alkylene groups, B and B' are, independently from each other, imino groups, substituted imino groups, oxy groups, thio groups, carbonyl groups, cycloalkylene groups, cycloalkylidene groups, or substituted or unsubstituted arylene groups, and m, n, p and q are 0 or 1.

2. A chromene compound according to claim 1, wherein in the formulas (4) and (5), the groups represented by $R^7$, $R^8$ and $R^9$ are, independently from each other, alkylene groups having 1 to 6 carbon atoms, the groups represented by B and B' are, independently from each other, imino groups, substituted imino groups, oxy groups, cycloalkylene groups, cycloalkylidene groups, or substituted or unsubstituted arylene groups.

3. A chromene compound according to claim 1, wherein the trivalent cyclic group represented by the formula (2) or (3) is:

(a) a substituted or unsubstituted aromatic hydrocarbon group comprising one benzene ring or a condensed ring formed by the condensation of 2 to 4 benzene rings;

(b) an aromatic heterocyclic group comprising an aromatic heterocyclic ring selected from a 5-membered ring or a 6-membered ring containing oxygen atom, sulfur atom or nitrogen atom;

(c) a condensed heterocyclic ring in which the above aromatic heterocyclic ring which is the 5-membered ring or the 6-membered ring is condensed with a benzene ring or, further, with a heterocyclic ring; or (d) a condensed heterocyclic group in which the benzene ring is condensed with the above aromatic heterocyclic ring which is the 5-membered ring or the 6-membered ring.

4. A chromene compound according to claim 1, wherein the trivalent cyclic group represented by the formula (2) or (3) is an aromatic hydrocarbon group or an aromatic heterocyclic group having a substituent which is:

a hydroxyl group, an alkyl group, a cycloalkyl group; an alkoxy group, an aralkyl group, an aralkoxy group, an amino group, a substituted amino group, a cyano group, a nitro group, a substituted or unsubstituted aryl group, a substituted or unsubstituted heteroaryl group, a halogen atom, a halogenoalkyl group, a halogenoalkoxy group, a substituted or unsubstituted heterocyclic group having a nitrogen atom as a hetero atom and is bonded via the nitrogen atom, a condensed heterocyclic group in which the above heterocyclic group is condensed with an aromatic hydrocarbon ring or an aromatic heterocyclic ring;

or is a group represented by the following formula (6)

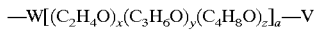

wherein W is —C(=O)O—, —CH$_2$O—, —OC(=O)—, —N(R$^a$)C(=O)—, —N[C(=O)—]$_2$, —N(R$^a$)—, —N(R$^a$)CON(H)—, >N—, an oxygen atom or a sulfur atom, x, y and z are integers of 0 to 50, the total number of x, y and z is 1 to 50, a is 1 when W is —C(=O)O—, —CH$_2$O—, —OC(=O)—, —N(R$^a$)C(=O)—, —N(R$^a$)—, —N(R$^a$)CON(H)—, an oxygen atom or a sulfur atom, and is 2 when W is —N[C(=O)—]$_2$ or >N—, V is a hydrogen atom, a (meth)acryloyl group, a group having an epoxy group with 1 to 5 carbon atoms, a group having a carboxyl group with 1 to 5 carbon atoms, an oxorane group, an aminoalkyl group with 1 to 6 carbon atoms or an oxylanylmethyl group, and Ra is a hydrogen atom or an alkyl group having 1 to 20 carbon atoms;

or is a group represented by the following formula (7)

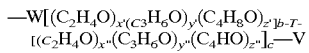

wherein, T is a divalent organic residue having 5 to 20 carbon atoms and containing a cyclic group, W and V are as defined in the formula (6), and x', y', z', x", y" and z" are the same as x, y and z in the formula (6).

5. A chromene compound according to claim 1, wherein R$^1$, R$^2$, R$^3$ and R$^4$ are, independently from each other, hydrogen atoms, alkyl groups, alkoxy groups, or halogenoalkyl groups.

6. A chromene compound according to claim 1, wherein R$^1$ and R$^2$ together and/or R$^3$ and R$^4$ together form rings.

7. A chromene compound according to claim 1, wherein either R$^1$ or R$^2$ and either R$^3$ or R$^4$ together form a ring.

8. A chromene compound according to claim 1, wherein R$^5$ and R$^6$ are substituted aryl groups or substituted heteroaryl groups, and said substitutent is a hydroxyl group, an alkyl group, a cycloalkyl group, an alkoxy group, an aralkyl group, an aralkoxy group, an amino group, a substituted amino group, a cyano group, a nitro group, a substituted or unsubstituted aryl group, a substituted or unsubstituted heteroaryl group, a halogen atom, a halogenoalkyl group, a halogenoalkoxy group, a substituted or unsubstituted heterocyclic group having a nitrogen atom as a hetero atom and is bonded via the nitrogen atom, a condensed heterocyclic group in which the above heterocyclic group is condensed with an aromatic hydrocarbon ring or an aromatic heterocyclic ring.

9. A chromene compound according to claim 1, wherein at least either R$^5$ or R$^6$ is:

(i) an unsubstituted aryl group;

(ii) a substituted aryl group having, as a substituent, substituted amino group, alkyl group, cycloalkyl group or alkoxy group;

(iii) a substituted aryl group in which the substituent is a heterocyclic group having a nitrogen as a hetero atom and is bonded to the aryl group via the nitrogen atom; or (iv) the substituted aryl group of (iii) above in which a heterocyclic group which is the substituent is forming a condensed heterocyclic group being condensed with the aromatic hydrocarbon ring or the aromatic heterocyclic ring.

10. A photochromic material comprising a chromene compound of claim 1.

11. A photochromic optical material containing a chromene compound of claim 1.

* * * * *